United States Patent [19]

Fischer et al.

[11] Patent Number: 5,763,676
[45] Date of Patent: Jun. 9, 1998

[54] PREPARATION OF AROMATIC ALDEHYDES

[75] Inventors: Rolf Fischer; Matthias Irgang, both of Heidelberg; Werner Schnurr, Herxheim; Joachim Wulff-Döring, Frankenthal, all of Germany

[73] Assignee: BASF Aktiengesellschaft, Ludwigshafen, Germany

[21] Appl. No.: 793,055

[22] PCT Filed: Aug. 10, 1995

[86] PCT No.: PCT/EP95/03167

§ 371 Date: Feb. 14, 1997

§ 102(e) Date: Feb. 14, 1997

[87] PCT Pub. No.: WO96/05161

PCT Pub. Date: Feb. 22, 1996

[30] Foreign Application Priority Data

Aug. 16, 1994 [DE] Germany ............ 44 28 994.4
Dec. 22, 1994 [DE] Germany ............ 44 46 009.0

[51] Int. Cl.⁶ .................................................. C07C 45/41
[52] U.S. Cl. ...................... 568/435; 502/308; 502/324; 502/325

[58] Field of Search ............... 568/435; 502/308, 502/324, 325

[56] References Cited

U.S. PATENT DOCUMENTS 4,328,373  5/1982  Strojny ......................... 568/435
4,613,700  9/1986  Maki et al. ..................... 568/435

*Primary Examiner*—Gary Geist
*Assistant Examiner*—Sreeni Padmanabhan
*Attorney, Agent, or Firm*—John H. Shurtleff

[57] ABSTRACT

Aromatic aldehydes are prepared by catalytically reacting aromatic carboxylic acids or their esters with hydrogen in the gas phase at from 200° to 450° C. and from 0.1 to 20 bar in the presence of a zirconium dioxide/lanthanide catalyst having a high BET surface area of from 20 to 150 m²/g, preferably from 40 to 150 m²/g. The proportions by weight of the catalytically active mass range from 80 to 99.9% by weight of zirconium dioxide and from 0.01 to 20 %by weight of one or more lanthanide elements. This catalyst provides very high conversion rates of 94 to 100% together with a correspondingly high selectivity for the aldehyde product.

15 Claims, No Drawings

PREPARATION OF AROMATIC ALDEHYDES

This is the U.S. National Stage Application of PCT/EP95/03167 filed Aug. 10, 1995 now WO96/05161 published Feb. 22, 1996.

The present invention relates to a process for preparing aromatic aldehydes by reaction of appropriate carboxylic acids or their esters with hydrogen in the gas phase in the presence of zirconium oxide and lanthanide element-containing catalysts.

It is known to convert carboxylic acids such as benzoic acid or cyclohexanecarboxylic acid or their esters into the corresponding aldehydes by hydrogenation in the gas phase.

U.S. Pat. No. 3,935,265 discloses that alkyl esters of aromatic carboxylic acids can be hydrogenated at from 400° to 600° C. on $Al_2O_3$ using hydrogen. For example, methyl benzoate is reacted with a selectivity of 37% (conversion: 39%) to give benzaldehyde. Ru/Sn (EP-A-539 274), manganese oxide (EP-A-290,096, U.S. Pat. No. 4,585,899), iron oxide (EP-A-304 853), vanadium oxide and/or titanium dioxide (U.S. Pat. No. 4,950,799, EP-A-414 065), $Cu/Y_2O_3$ (U.S. Pat. No. 4,585,900), $Cr_2O_3/ZrO_2$ (EP-A-150 961), or lanthanide oxides/$Al_2O_3$ catalysts (U.S. Pat. No. 4,328,373, EP-A-101 111), for example, are furthermore employed for the hydrogenation of aromatic carboxylic acids.

In the known hydrogenation processes, in most cases, partly as a result of very high hydrogenation temperatures, only unsatisfactory yields and selectivities are achieved.

It is an object of the present invention to remedy the above-mentioned disadvantages.

We have now found that this object is achieved by a novel and improved process for preparing aromatic aldehydes of the general formula I

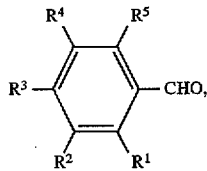

(I)

where $R^1$, $R^2$, $R^3$, $R^4$ and $R^5$ are hydrogen, $C_1$- to $C_6$-alkyl, $C_3$- to $C_8$-cycloalkyl, aryl, hydroxyl, $C_1$- to $C_4$-alkoxy, phenoxy, $C_7$- to $C_{12}$-alkylphenyl, $C_7$- to $C_{12}$-phenylalkyl, amino, methylamino, dimethylamino or halogen and $R^2$, $R^3$ or $R^4$ is additionally formyl or $COOR^6$ $R^6$ is hydrogen, $C_1$- to $C_6$-alkyl, $C_3$- to $C_8$-cycloalkyl, aryl, $C_7$- to $C_{12}$-alkylphenyl or $C_7$- to $C_{12}$-phenylalkyl, which comprises reacting aromatic carboxylic acids or their esters of the general formula II

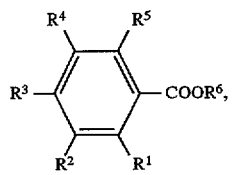

(II)

where $R^1$, $R^2$, $R^3$, $R^4$, $R^5$ and $R^6$ have the abovementioned meanings or where $R^2$, $R^3$, $R^4$ and $R^5$ have the abovementioned meanings and $R^6$ and $R^1$ together form a —$CH_2$— bridge, with hydrogen in the gas phase at from 200° to 450° C. and from 0.1 to 20 bar in the presence of a catalyst, whose catalytically active mass contains from 80 to 99.9% by weight of zirconium oxide and from 0.1 to 20% by weight of one or more lanthanide elements.

The process according to the invention can be carried out as follows:

The hydrogenation according to the invention of the aromatic carboxylic acids or their esters II with hydrogen in the presence of a catalyst whose catalytically active mass contains from 60 to 99.9, in particular from 80 to 99.9,% by weight of zirconium oxide and from 0.1 to 40, in particular from 0.1 to 20, % by eight of one or more lanthanide elements, is as a rule carried out at from 200° to 450° C., preferably from 250° to 400° C., particularly preferably from 300° to 380° C., and from 0.1 to 20 bar, preferably from 0.7 to 5 bar, particularly preferably atmospheric pressure (normal pressure). The required temperature and the required pressure are dependent on the catalyst activity and the thermal stability of starting material and product.

Suitable catalysts are supported catalysts, but preferably unsupported catalysts of zirconium oxide in cubic, tetragonal or monoclinic phase, preferably in monoclinic phase, which are preferably doped with one or more elements from the lanthanide series. As a rule, the catalytically active mass contains from 80 to 99.9% by weight, preferably from 90 to 99.9% by weight, particularly preferably from 92 to 99% by weight, of zirconium oxide and from 0.1 to 20% by weight of one or more lanthanide elements, preferably from 0.1 to 10% by weight of lanthanum, cerium, praseodymium, neodymium, samarium, europium or mixtures thereof, particularly preferably from 1 to 8% by weight of lanthanum (III) oxide. As a rule, doping is carried out by impregnating the zirconium oxide with salt solutions (aqueous or alcoholic) of the lanthanides.

The catalyst can additionally contain further dopants (eg. chromium, iron, yttrium, manganese) in amounts from 0.001 to 10% by weight. Catalysts without such additions are preferred.

The BET surface area of the zirconium oxide can vary within wide limits, and as a rule is from 5 to 150 $m^2/g$, preferably from 20 to 150 $m^2/g$, particularly preferably from 40 to 120 $m^2/g$.

Catalysts of this type are prepared in a known manner, eg. by impregnating preformed supports such as pellets, spheres or extrudates, drying and calcining.

The supported catalysts preferably used exhibit high activity over a relatively long period. Deactivated catalysts can be regenerated by treatment with gases containing molecular oxygen, eg. air, at from 350° to 500° C.

In general, a catalyst loading of from 0.01 to 10, preferably from 0.01 to 3 kg, of carboxylic acid (ester) per kg of catalyst per hour is kept to.

The hydrogen concentration in the inlet gas depends on the carboxylic acid (ester) concentration. As a rule, the molar ratio of hydrogen to carboxylic acid (ester) is from 2:1 to 100:1, preferably from 10:1 to 70:1. Formic acid can also be employed as a source of hydrogen.

The addition of an inert diluent can also be advantageous. As a rule, nitrogen, water or gaseous compounds which are inert under the reaction conditions, such as eg. hydrocarbons, aromatics or ethers, are used.

The reaction can be carried out in the gas phase, continuously as a solid bed reaction with a fixed-bed catalyst, for example in a liquid phase or trickle-bed procedure or as a fluidized bed reaction with a fluidized catalyst. Working in a solid bed is preferred.

To increase the selectivity, by-products formed in the hydrogenation, eg. alcohols, can be fed back into the synthesis.

The substituents $R^1$, $R^2$, $R^3$, $R^4$, $R^5$ and $R^6$ in the compounds I and II independently of one another have the following meanings:

$R^1$, $R^2$, $R^3$, $R^4$, $R^5$ and $R^6$ hydrogen, $C_1$- to $C_6$-alkyl, preferably $C_1$- to $C_4$-alkyl such as methyl, ethyl, n-propyl, isopropyl, n-butyl, isobutyl, sec-butyl and tert-butyl, particularly preferably methyl and ethyl, $C_3$- to $C_8$-cycloalkyl such as cyclopropyl, cyclobutyl, cyclopentyl, cyclohexyl, cycloheptyl and cyclooctyl, preferably cyclopentyl, cyclohexyl and cyclooctyl, particularly preferably cyclopentyl and cyclohexyl, aryl such as phenyl, 1-naphthyl, 2-naphthyl, 1-anthryl, 2-anthryl and 9-anthryl, preferably phenyl, 1-naphthyl and 2-naphthyl, particularly preferably phenyl, $C_7$- to $C_{12}$-alkylphenyl such as 2-methylphenyl, 3-methylphenyl, 4-methylphenyl, 2,4-dimethylphenyl, 2,5-dimethylphenyl, 2,6-dimethylphenyl, 3,4-dimethylphenyl, 3,5-dimethylphenyl, 2,3,4-trimethylphenyl, 2,3,5-trimethylphenyl, 2,3,6-trimethylphenyl, 2,4,6-trimethylphenyl, 2-ethylphenyl, 3-ethylphenyl, 4-ethylphenyl, 2-n-propylphenyl, 3-n-propylphenyl and 4-n-propylphenyl, preferably 2-methylphenyl, 3-methylphenyl, 4-methylphenyl, 2,4-dimethylphenyl, 2,5-dimethylphenyl, 2,6-dimethylphenyl, 3,4-dimethylphenyl and 3,5-dimethylphenyl, particularly preferably 2-methylphenyl, 3-methylphenyl, 4-methylphenyl, $C_7$- to $C_{12}$-phenylalkyl such as benzyl, 1-phenethyl, 2-phenethyl, 1-phenylpropyl, 2-phenylpropyl, 3-phenylpropyl, 1-phenylbutyl, 2-phenylbutyl, 3-phenylbutyl and 4-phenylbutyl, preferably benzyl, 1-phenethyl and 2-phenethyl, particularly preferably benzyl, $R^2$, $R^3$ and $R^4$ hydroxyl, $C_1$- to $C_4$-alkoxy such as methoxy, ethoxy, n-propoxy, isopropoxy, n-butoxy, isobutoxy, sec-butoxy and tert-butoxy, preferably methoxy, ethoxy, n-propoxy and isopropoxy, particularly preferably methoxy and ethoxy, phenoxy, amino, methylamino, dimethylamino, halogen such as fluorine, chlorine, bromine and iodine, preferably fluorine, chlorine and bromine, particularly preferably chlorine and bromine, and $R^2$, $R^3$ or $R^4$ formyl (—CHO) or $COOR^6$.

In formula II, $R^6$ and $R^1$ can furthermore together form a —$CH_2$— bridge.

Any desired substitution pattern is possible, ie. the substituents can be located, for example, either in the 2,3,4-, 2,3,5-, 2,3,6-, 3,4,5-, 3,4,6-, or the 4,5,6-position.

Starting substances used are aromatic mono- or dicarboxylic acids or carboxylic acid esters II, eg. benzoic acid (esters), terephthalic acid (esters), phthalic acid (esters), i-phthalic acid (esters), alkyl-substituted, alkoxy-substituted, dialkyl-substituted or alkoxyalkyl-substituted carboxylic acids (esters). Esters employed are preferably methyl, ethyl, propyl, isopropyl, butyl, isobutyl, tert-butyl, cyclopentyl, cyclohexyl, phenyl and benzyl esters. Particularly preferred compounds are benzoic acid, terephthalic acid, phthalic acid, 2-, 3- and 4-methylbenzoic acid, 4-isopropylbenzoic acid, 4-tert-butylbenzoic acid, 4-methoxybenzoic acid, phthalide, vanillic acid and the respective methyl esters.

In the hydrogenation of dicarboxylic acids (esters), aldehyde carboxylic acids (esters) are formed first, which, if desired, are also used as intermediates. The maximum aldehydecarboxylic acid (ester) yield is obtained in the case of incomplete conversion.

When conversion is increased, dialdehyde formation is preferably observed as a result of further hydrogenation.

With the aid of the process according to the invention it is possible to prepare aldehydes which were previously accessible with difficulty selectively in a simple manner.

The aldehydes I are suitable as aromatizers and flavorings or as intermediates, eg. for pharmaceutical and crop protection active compounds (Ullmann's Encyclopedia of Industrial Chemistry, Vol. A3, pp. 469–74).

EXAMPLES

Catalyst Preparation

Example 1

Monoclinic zirconium dioxide (BET surface area: 40 to 85 $m^2/g$) in the form of tablets (catalyst A, E or F) or extrudates (catalyst B, C or D) was impregnated with an aqueous solution of the lanthanide element nitrate (or of the lanthanide element nitrates) with thorough mixing and kept at room temperature for 2 h. The catalyst was then dried at 120° C. for 15 hours and then temperature controlled at from 400° to 500° C. for from 2 to 4 hours.

The catalysts thus obtained had the following lanthanide content:

Catalyst A (surface area 67 $m^2/g$): 3% by weight of lanthanum

Catalyst B (surface area 46 $m^2/g$): 3% by weight of praseodymium

Catalyst C (surface area 46 $m^2/g$): 3% by weight of cerium

Catalyst D (surface area 46 $m^2/g$): 3% by weight of lanthanides (Distribution: 48% $CeO_2$, 26.3% $La_2O_3$, 5.7% $Pr_2O_3$ and 19.7% $Nd_2O_3$).

Catalyst E (surface area 85 $m^2/g$): 3% by weight of lanthanum

Catalyst F (surface area 53 $m^2/g$): 3% by weight of lanthanum

Example 2

From 4 to 8 g of aromatic carboxylic acid (ester) II per hour were passed with or without solvent (THF) into an evaporator (<300° C.) and from there passed with 100 l/h of hydrogen over 100 g of catalyst in a trickle-bed procedure. The gaseous material discharged from the reaction was condensed in cold traps and analyzed by gas chromatography. The results are summarized in Table 1.

Example 3

6 g of dimethyl terephthalate (as a melt) per hour were evaporated using 100 l/h of hydrogen and passed at 350° C. over 100 g of catalyst E in a trickle-bed procedure. The gaseous material discharged from the reaction was condensed in cold traps and analyzed by gas chromatography. The main products obtained were 32% of terephthalaldehyde and 27% of methyl 4-formylbenzoate (conversion: 78%).

Example 4

8 g of 2-methylbenzoic acid (as a melt) per hour were evaporated using 200 l/h of hydrogen and passed at 350° C.

over 100 g of catalyst F in a trickle-bed procedure. The gaseous material discharged from the reaction was condensed in cold traps and analyzed by gas chromatography. The yield of 2-methylbenzaldehyde was 93% (conversion: 99%).

Example 5

5 g of 3-methylbenzoic acid (as a melt) per hour were evaporated using 100 l/h of hydrogen and passed at 360° C. over 100 g of catalyst F in a trickle-bed procedure. The gaseous material discharged from the reaction was condensed in cold traps and analyzed by gas chromatography. The yield of 3-methylbenzaldehyde was 92% (conversion: 99%).

Example 6

8 g of phthalide (as a melt) per hour were evaporated using 100 l/h of hydrogen and passed at 400° C. over 100 g of catalyst F in a trickle-bed procedure. The gaseous material discharged from the reaction was condensed in cold traps and analyzed by gas chromatography. The yield of 2-methylbenzaldehyde was 16% (conversion: 26%).

TABLE 1

Starting compound: R—⟨phenyl⟩—COOH

| Catalyst | R | Conc. of the carboxylic acid [% by weight][1) | Temperature [°C.] | Aldehyde [%] | Conversion [%] | Selectivity [%] |
|---|---|---|---|---|---|---|
| A | H | 100 | 340 | 98 | 100 | 98 |
| A | H | 20 | 350 | 98 | 100 | 98 |
| A | Me | 100 | 340 | 96 | 99 | 97 |
| A | t-Bu | 100 | 340 | 90 | 94 | 96 |
| A | t-Bu | 20 | 340 | 93 | 97 | 96 |
| A | OMe | 10 | 350 | 77 | 99 | 78 |
| B | H | 100 | 360 | 95 | 100 | 95 |
| C | H | 100 | 360 | 96 | 100 | 96 |
| D | H | 100 | 360 | 97 | 99 | 98 |
| F | i-Pr | 100 | 350 | 90 | 98 | 92 |

We claim:

1. In a process of preparing aromatic aldehydes by catalytically reacting aromatic carboxylic acids or their esters with hydrogen in the gas phase at from 200° to 450° C. and from 0.1 to 20 bar, the improvement which comprises carrying out the reaction in the presence of a solid catalyst whose BET surface area is from 20 to 150 m²/g and whose catalytically active mass contains from 80 to 99.9% by weight of zirconium dioxide and from 0.1 to 20% by weight of one or more lanthanide elements.

2. A process as claimed in claim 1 for preparing aromatic aldehydes of the formula I

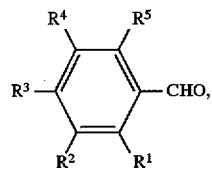

where $R^1$, $R^2$, $R^3$, $R^4$ and $R^5$ are hydrogen, $C_1$- to $C_6$-alkyl, $C_3$- to $C_8$-cycloalkyl, aryl, hydroxyl, $C_1$- to $C_4$-alkoxy, phenoxy, $C_7$- to $C_{12}$-alkylphenyl, $C_7$- to $C_{12}$-phenylalkyl, amino, methylamino, dimethylamino or halogen and $R^2$, $R^3$ or $R^4$ is additionally formyl or $COOR^6$ $R^6$ is hydrogen, $C_1$- to $C_6$-alkyl, $C_3$- to $C_8$-cycloalkyl, aryl, $C_7$- to $C_{12}$-alkylphenyl or $C_7$- to $C_{12}$-phenylalkyl, which comprises reacting aromatic carboxylic acids or their esters of the formula II

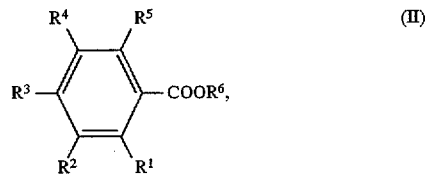

where $R^1$, $R^2$, $R^3$, $R^4$, $R^5$ and $R^6$ have the abovementioned meanings or where $R^2$, $R^3$, $R^4$ and $R^5$ have the abovementioned meanings and $R^6$ and $R^1$ together form a —$CH_2$— bridge.

3. A process as claimed in claim 1, wherein the catalyst contains as the catalytically active mass from 90 to 99.9% by weight of zirconium oxide and as the lanthanide element from 0.1 to 10% by weight of lanthanum, cerium, praseodymium, neodymium, samarium, europium or mixtures thereof.

4. A process as claimed in claim 1, wherein the catalyst contains as the catalytically active mass from 92 to 99% by weight of zirconium oxide and from 1 to 8% by weight of lanthanum(III) oxide.

5. A process as claimed in claim 1, wherein the zirconium dioxide is monoclinic.

6. A process as claimed in claim 1, wherein benzoic acid, 2-methylbenzoic acid, 3-methylbenzoic acid, 4-methylbenzoic acid, 4-isopropylbenzoic acid, 4-methoxybenzoic acid, phthalide or terephthalic acid or their esters are hydrogenated to give the corresponding mono- or dialdehyde.

7. A process as claimed in claim 1, the molar ratio of hydrogen to carboxylic acid (ester) is from 2:1 to 100:1.

8. A process as claimed in claim 1, wherein the reaction is carried out in a solid bed.

9. A process as claimed in claim 1, wherein said solid catalyst has a BET surface area of from 40 to 120 m²/g.

10. A process as claimed in claim 9, wherein said solid catalyst as the catalytically active mass contains from 92 to 99% by weight of zirconium dioxide and from 2 to 8% by weight of at least one lanthanide element selected from the group consisting of lanthanum, cerium, praseodymium, neodymium, samarium and europium.

11. A process as claimed in claim 10, wherein said solid catalyst consists essentially of zirconium dioxide and lanthanum.

12. A process as claimed in claim 10, wherein said solid catalyst consists essentially of zirconium dioxide and cerium.

13. A process as claimed in claim 10, wherein said solid catalyst consists essentially of zirconium dioxide and praseodymium.

14. A process as claimed in claim 1, wherein the process is carried out continuously at temperatures of from 250° to 400° C. and pressures of from 0.7 to 5 bar.

15. A process as claimed in claim 1, wherein the process is carried out continuously at temperatures of from 300° to 380° C. and atmospheric pressure.

* * * * *